(12) United States Patent
Obst et al.

(10) Patent No.: US 11,426,302 B2
(45) Date of Patent: Aug. 30, 2022

(54) CONTAINMENT DEVICES FOR TREATMENT OF INTESTINAL FISTULAS AND COMPLEX WOUNDS

(71) Applicant: Fistula Solution Corporation, Scandia, MN (US)

(72) Inventors: Andrew Thomas Obst, Scandia, MN (US); Maryanne Obst, Scandia, MN (US)

(73) Assignee: FISTULA SOLUTION CORPORATION, Scandia, MN (US)

( * ) Notice: Subject to any disclaimer, the term of this patent is extended or adjusted under 35 U.S.C. 154(b) by 275 days.

(21) Appl. No.: 16/883,559

(22) Filed: May 26, 2020

(65) Prior Publication Data

US 2020/0297523 A1    Sep. 24, 2020

Related U.S. Application Data

(63) Continuation-in-part of application No. 14/931,204, filed on Nov. 3, 2015, now Pat. No. 10,660,786.

(60) Provisional application No. 62/122,965, filed on Nov. 3, 2014.

(51) Int. Cl.
*A61F 5/443* (2006.01)
*A61M 1/00* (2006.01)

(52) U.S. Cl.
CPC .............. *A61F 5/443* (2013.01); *A61M 1/90* (2021.05)

(58) Field of Classification Search
CPC ........ A61F 5/443; A61F 5/445; A61M 1/0088
See application file for complete search history.

(56) References Cited

U.S. PATENT DOCUMENTS 3,398,744 A * 8/1968 Hooper ................... A61F 5/445
604/340
5,015,244 A    5/1991 Cross
5,429,626 A    7/1995 Fenton
(Continued)

FOREIGN PATENT DOCUMENTS

EP              3406275 A1    11/2018
WO     WO 03/045492 A1    6/2003
(Continued)

OTHER PUBLICATIONS

Aguila III D.J., et al., "The Stool Shield: A Novel Approach to the Colo-Atmospheric Fistula," Journal of the American College of Surgeons, Sep. 2011, vol. 213 (3), pp. e17-e20.
(Continued)

*Primary Examiner* — Guy K Townsend
(74) *Attorney, Agent, or Firm* — Patterson Thuente Pedersen, P.A.

(57) ABSTRACT

Devices to contain and control the effluent or gastric juices of intestinal fistulas, other fistulas, stomas, and other wounds. The device includes a flexible fluid containment lineal strip defining a fluid containment wall which collapses when pressure is applied to the wound dressing, means for forming the lineal strip into any open or closed shape to fit wounds of various shape and size, means for joining the lineal strip to create closed effluent containment areas, means for creating a seal at the wound bed interface whereby effluent is contained, and means for interfacing with a pouch appliance to capture effluent and bowel contents until bowel contents can be emptied into a toilet or other waste receptacle.

20 Claims, 11 Drawing Sheets

(56) References Cited

U.S. PATENT DOCUMENTS

| | | | |
|---|---|---|---|
| 5,636,643 | A | 6/1997 | Argenta et al. |
| 5,738,661 | A | 4/1998 | Larice |
| 6,099,508 | A | 8/2000 | Bousquet |
| 6,709,421 | B1* | 3/2004 | Falconer ................ A61F 5/445 604/335 |
| 6,765,122 | B1 | 7/2004 | Stout |
| 7,147,627 | B2 | 12/2006 | Kim et al. |
| 7,160,275 | B2* | 1/2007 | Falconer ................ A61F 5/445 604/338 |
| 7,708,724 | B2 | 5/2010 | Weston |
| 8,167,857 | B2 | 5/2012 | James |
| 8,409,157 | B2* | 4/2013 | Haggstrom ....... A61F 13/00068 604/315 |
| 8,529,526 | B2* | 9/2013 | Wilkes .................. A61M 1/732 604/289 |
| 8,758,314 | B2* | 6/2014 | Hall ........................ A61F 5/445 604/319 |
| 8,915,894 | B1* | 12/2014 | Lonky .................... A61M 1/90 604/289 |
| 9,078,990 | B1 | 7/2015 | Obst et al. |
| 9,265,665 | B2* | 2/2016 | Robinson ................ A61F 13/02 |
| 9,629,743 | B2* | 4/2017 | Grum-Schwensen ...................... A61F 5/443 |
| 9,782,328 | B2 | 10/2017 | Gutwein et al. |
| 10,182,947 | B2* | 1/2019 | Hu ........................ A61M 1/912 |
| 10,660,786 | B2* | 5/2020 | Obst ........................ A61F 5/445 |
| 2005/0015065 | A1* | 1/2005 | Falconer ................ A61F 5/441 604/335 |
| 2007/0191794 | A1* | 8/2007 | Cline ........................ A61F 5/445 604/335 |
| 2008/0161778 | A1* | 7/2008 | Steward ................ A61M 27/00 604/543 |
| 2008/0269700 | A1 | 10/2008 | O'Toole et al. |
| 2008/0287892 | A1* | 11/2008 | Khan ........................ A61M 1/90 604/289 |
| 2008/0319397 | A1 | 12/2008 | MacAluso |
| 2009/0131893 | A1 | 5/2009 | Priest et al. |
| 2009/0192467 | A1 | 7/2009 | Hansen et al. |
| 2009/0209917 | A1 | 8/2009 | Tanaka et al. |
| 2009/0227969 | A1* | 9/2009 | Jaeb ........................ A61M 1/962 604/313 |
| 2010/0145293 | A1* | 6/2010 | Verhaalen ................ A61F 5/445 604/337 |
| 2010/0262095 | A1* | 10/2010 | Hall ........................ A61M 1/86 604/319 |
| 2010/0280489 | A1 | 11/2010 | Nishtala et al. |
| 2010/0312192 | A1 | 12/2010 | Fitzgerald et al. |
| 2011/0040269 | A1* | 2/2011 | Cline ........................ A61F 5/445 604/335 |
| 2011/0137270 | A1* | 6/2011 | Hu ........................ A61M 1/732 604/319 |
| 2011/0213287 | A1* | 9/2011 | Lattimore ................ A61M 1/90 604/319 |
| 2012/0029450 | A1* | 2/2012 | Grum-Schwensen ...................... A61F 5/443 604/344 |
| 2012/0101458 | A1* | 4/2012 | Hall ........................ A61M 1/90 604/319 |
| 2012/0130187 | A1 | 5/2012 | Okoniewski |
| 2012/0232505 | A1 | 9/2012 | Eskaros et al. |
| 2014/0148771 | A1* | 5/2014 | Luce ........................ A61F 5/448 604/345 |
| 2014/0207027 | A1* | 7/2014 | Navia ................ A61F 13/00068 604/319 |
| 2014/0221946 | A1* | 8/2014 | Croizat ............. A61F 13/00068 604/319 |
| 2014/0309604 | A1* | 10/2014 | Paratore ................ A61F 5/4407 604/332 |
| 2014/0324002 | A1* | 10/2014 | Luce ........................ A61F 5/441 604/338 |
| 2015/0100045 | A1* | 4/2015 | Allen .................... F04B 45/047 604/543 |
| 2015/0209492 | A1* | 7/2015 | Blott ........................ A61M 27/00 604/319 |
| 2016/0120687 | A1* | 5/2016 | Obst ........................ A61F 5/445 604/337 |
| 2016/0120706 | A1* | 5/2016 | Collinson ............. A61M 1/913 604/319 |
| 2016/0287428 | A1 | 10/2016 | Eggert et al. |
| 2017/0361069 | A1 | 12/2017 | Gazzani Romolo et al. |
| 2017/0367871 | A1 | 12/2017 | Dinakara et al. |
| 2019/0046698 | A1* | 2/2019 | Loske ............... A61F 13/00059 |
| 2020/0253633 | A1 | 8/2020 | Andrew et al. |
| 2020/0405523 | A1 | 12/2020 | Andrew et al. |

FOREIGN PATENT DOCUMENTS

| | | |
|---|---|---|
| WO | WO-2004084778 A2 | 10/2004 |
| WO | WO-2009049232 A1 | 4/2009 |
| WO | WO-2010075032 A2 | 7/2010 |
| WO | WO-2011015203 A1 | 2/2011 |
| WO | WO-2011031822 A1 | 3/2011 |
| WO | WO-2011138727 A1 | 11/2011 |
| WO | WO-2014140606 A1 | 9/2014 |
| WO | WO 2019/136164 A1 | 7/2019 |

OTHER PUBLICATIONS

Application and File history for U.S. Appl. No. 16/275,029, filed Feb. 13, 2019, inventors Obst et al.

Application and File History for U.S. Appl. No. 14/931,204, filed Nov. 3, 2015, inventors Obst, et al.

Application and File History for U.S. Appl. No. 13/750,154, filed Jan. 25, 2013, inventors Obst et al.

Application and File history for U.S. Appl. No. 16/453,315, filed Jun. 26, 2019, inventors Obst, et al.

Byrnes M.C., et al., "A Novel Technique to Skin Graft Abdominal Wall Wounds Surrounding Enterocutaneous Fistulas," Surgical Infections, vol. 11 (6), Apr. 18-20, 2010, pp. 505-510.

Communication pursuant to Article 94(3) EPC for Application No. 15857923.5, dated Jan. 16, 2020, 5 pages. Need reference.

Extended European Search Report for Application No. 15857923.5, dated May 2, 2018, 9 pages.

Goverman J., et al., "The "Fistula VAC," a Technique for Management of Enterocutaneous Fistulae Arising within the Open Abdomen: Report of 5 Cases," The Journal of Trauma Injury, Infection, and Critical Care, Feb. 2006, vol. 60 (2), pp. 428-431.

International Preliminary Reporton Patentability for Application No. PCT/US2015/058740, dated May 18, 2017, 12 pages.Need reference.

International Search Report and Written Opinion for Application No. PCT/US2015/058740, dated Feb. 3, 2016, 16 pages.

Stremitzer S., et al., "Successful Bridging Treatment and Healing of Enteric Fistulae by Vacuum-Assisted Closure (VAC) Therapy and Targeted Drainage in Patients with Open Abdomen," International Journal of Colorectal Disease, vol. 26, Jan. 2011, pp. 661-666.

Application and File history for U.S. Appl. No. 16/883,559, filed May 26, 2020, inventors Obst et al.

European Search Report for European Application No. EP20157187.4 dated Jul. 14, 2020, 11 pages.

Extended Search Report dated Mar. 1, 2021 for EP Application No. 20201280.3, 8 pages.

* cited by examiner

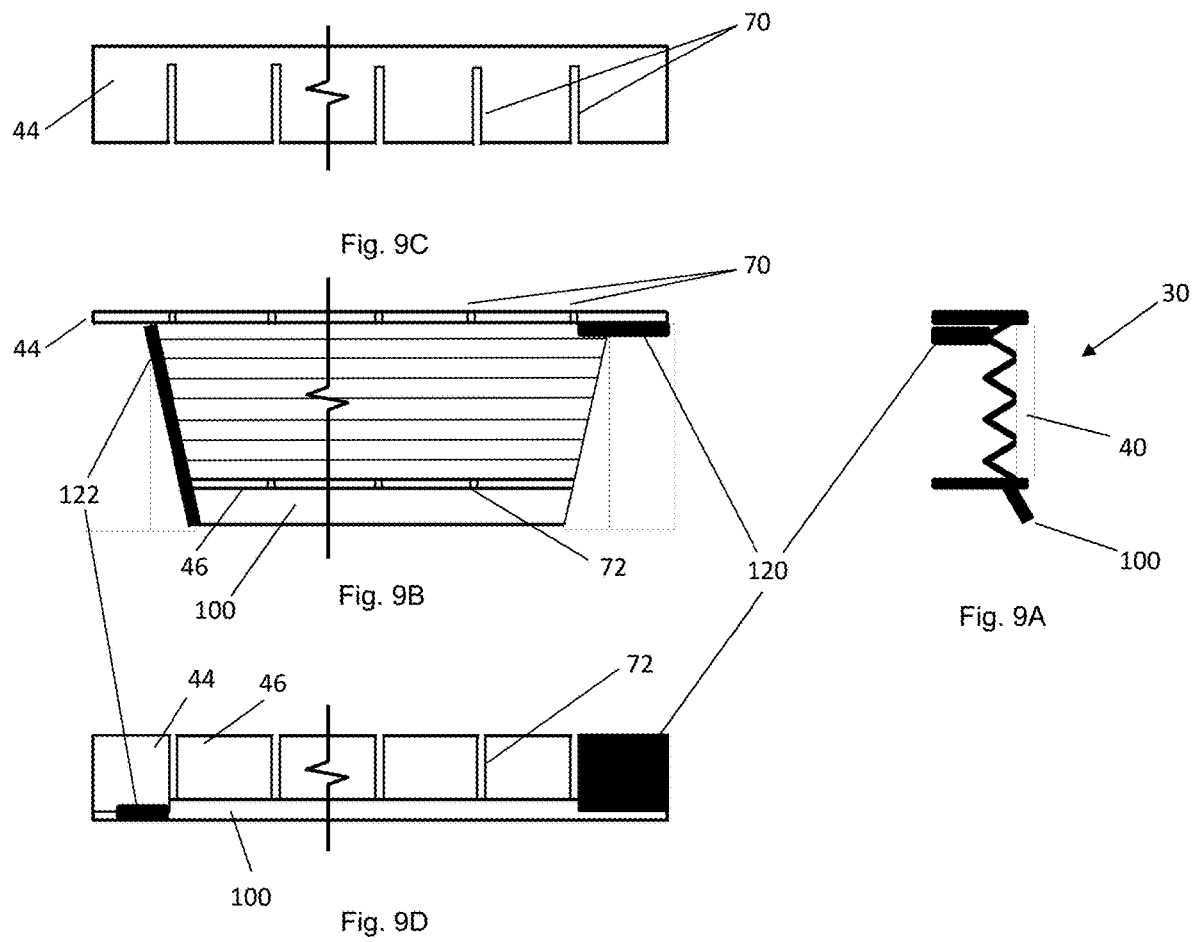

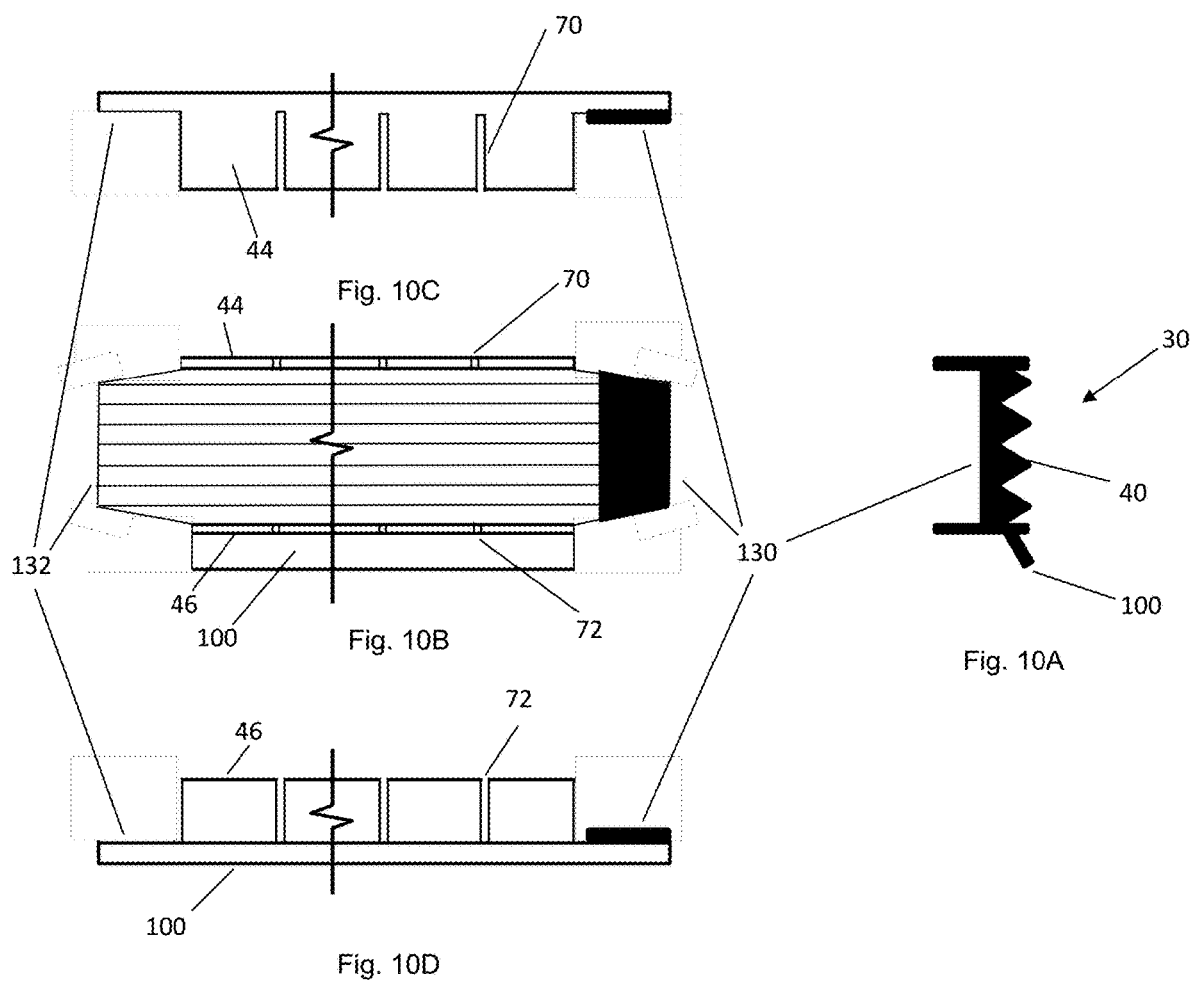

CONTAINMENT DEVICES FOR TREATMENT OF INTESTINAL FISTULAS AND COMPLEX WOUNDS

RELATED APPLICATIONS

This application is a continuation-in-part of application Ser. No. 14/931,204 filed Nov. 3, 2015, which the benefit of U.S. Provisional Application No. 62/122,965 filed Nov. 3, 2014, each of which is hereby incorporated herein in its entirety by reference.

BACKGROUND OF THE INVENTION

Complex abdominal wound care presents many challenges for healthcare professionals and patients. Particularly difficult to manage are enteric or intestinal fistulas which drain the contents of the bowel into open abdominal wounds. Fistulas are abnormal passages between organs that do not normally connect. In cases of intestinal fistulas, a passage from the intestines to the surface of the skin allows intestinal contents or effluent to spill onto a wound site and surrounding skin leading to infection, persistent tissue inflammation, and potentially sepsis. An intestinal fistula can produce seven liters or more of intestinal effluent per day that must be contained and controlled if the wound is to heal.

Intestinal fistulas often lie within a much larger abdominal wound bed. Abdominal wounds with fistulas can encompass large areas of the abdomen, measuring 20 centimeters or greater in diameter and 6 cm or more in depth. Malnutrition, frequent infectious complications, chronic pain, and depression are common in patients with this overwhelming condition. Operative management often requires lengthy procedures of six to ten hours with high risk of morbidity and mortality. To achieve good outcomes, operative repairs generally need to occur six to twelve months after initial identification of the intestinal fistula. Because of the lengthy interval between presentation of the intestinal fistula and definitive surgical repair, intervening wound management takes on a unique importance.

Negative Pressure Wound Therapy (NPWT) uses a vacuum source to compress wound filler dressings and is commonly applied to complex abdominal wounds to promote healing. NPWT holds promise in managing open wounds with intestinal fistulas; however the effectiveness of NPWT and other wound therapies have been limited by a persistent problem of wound filler dressing failure due to intestinal fistula effluent or gastric juice fouling. As a NPWT vacuum is applied to a wound bed that includes an intestinal fistula, the fistula's effluent is drawn into the NPWT wound filler dressing and across the entire wound bed. The effluent contamination causes tissue breakdown and infection, creates a loss of dressing vacuum seal as the system is overwhelmed with effluent, and necessitates frequent changes of expensive NPWT wound filler dressings.

A number of devices have been proposed to control the effluent and bowel contents from intestinal fistulas, including U.S. patent publications 2010/0145293 to Verhaalen, 2008/0161778 to Steward, and 2008/0287892 to Khan et al.; however none of the references appears to have been commercialized in a way that has practical application at the bedside and intestinal fistula wound dressing failure remains a common problem.

General disadvantages found with the references include: 1. Devices are not adaptable to comprehend the broad spectrum of intestinal fistula and other wound types. Different stages of fistula development and healing have different effluent control demands that are difficult to address with devices that are not tailored to the specific wound. 2. Multi-component devices and multi-step device assembly create complexity for caregivers and may require specialized training or the expertise of a wound specialist. 3. Devices with rigid surfaces are very difficult to seal to the wound bed and are potentially dangerous to the intestine and adjacent tissue. Abdominal wound beds are dynamic and pliable surfaces and in practice we find that fistula effluent quickly finds its way past rigid devices and the wound dressing is fouled. Also, rigid devices tend to be uncomfortable for the patient and can aggravate the wound being treated. 4. Devices with thick containment walls and rigid flanges cannot be placed over fistulas and wounds that are in close proximity to the sides of the wound bed or underneath the edges of the abdominal wall and can cause tissue, intestinal, or other structural damage. 5. Devices that rely on ostomy adhesive to create a seal between the device and the wound site have poor longevity. In practice we find that these adhesives do not adhere to wet, weeping wound beds and adhesion generally fails. As adhesion is lost, fistula effluent is drawn past the device and wound dressing is fouled.

An embodiment of the "isolation component" described in U.S. patent publication 2010/0145293 is demonstrated online at http://www.youtube.com/watch?v=fOGpffzZvSY for use on intestinal fistula patients. However, this device has specific disadvantages. 1. The device is too complex for bedside nurses or homecare nurses to assemble without the help of a wound specialist. 2. The device fails to stay in the desired location when compressed with NPWT. 3. The device does not maintain desired form when compressed with NPWT and effluent is drawn past the device and wound dressing is fouled. 4. Caregivers often give up on the technique after repeated failures.

The present disclosure provides devices improved over the prior patent references and prior products.

SUMMARY

Embodiments according to the disclosure are directed to devices to contain and control the effluent or gastric juices of intestinal fistulas, other fistulas, stomas, and other wounds, comprises a flexible fluid containment lineal strip, fluid containment walls which collapse when pressure is applied to the wound dressing, means for forming the lineal strip into any open or closed shape to fit wounds of various shape and size, means for joining the lineal strip to create closed effluent containment areas, means for creating a seal at the wound bed interface whereby effluent is contained, and means for interfacing with a pouch appliance to capture effluent and bowel contents until bowel contents can be emptied into a toilet or other receptacle for disposing of waste.

Accordingly, this disclosure describes numerous intestinal fistula devices having various aspects and advantages. The disclosure provides devices, which are simple in construction, to contain and control the effluent and bowel content from intestinal fistulas, other fistulas, stomas, and other wounds so dressings can be applied and changed by nonspecialized bedside or homecare nurses. These devices seal to the wound bed and do not allow effluent to be drawn past the seal, even with negative pressure wound therapy (NPWT) or other wound care techniques, that might be used to extend dressing life and/or establish effective conditions for wound healing. The devices hold themselves in the intended location, even with the application of NPWT and/or other wound therapies, during normal daily activity of the patient. The devices mitigate the need for ostomy adhesive, which reduces the frequency of wound dressing changes due to ostomy adhesive failure. The devices can be custom cut (e.g., at bedside) to best fit the device to irregular surfaces of wound beds or isolate a fistula or wound that is in close proximity to the sides of the wound bed or underneath the edges of the abdominal wall. The devices are flexible and collapse symmetrically when part of NPWT or other wound therapy to prevent deformation or buckling over and related aggravation of the fistula, intestine, or wound. The devices isolate the intestinal fistula or wound from suction or vacuum, thus protecting the bowel or wound site from negative pressures. The devices are adaptable to a broad spectrum of intestinal fistula, ostomy, and other wound types. Overall, the devices improve the healing process and thus improve the quality of patient life, by allowing patients to return to their normal life and work routines during the healing process.

These and various other features and advantages will be apparent from a reading of the following detailed description.

BRIEF DESCRIPTION OF THE DRAWING

The invention may be more completely understood in consideration of the following detailed description of various embodiments of the invention in connection with the accompanying drawing, in which:

FIG. 9A is a cross-sectional elevantional view of an alternative embodiment of the device of FIG. 7A.

FIG. 9B is an elevational view of an exterior sidewall of the device of FIG. 9A showing a skin seal and a wound seal.

FIG. 9C is a top view of the device of FIG. 9A.

FIG. 9D is a bottom view of the device of FIG. 9A showing a skin seal and a wound seal.

FIG. 10A is a cross-sectional elevational view of an alternative embodiment of the device of FIG. 7A.

FIG. 10B is an elevational view of an exterior sidewall of the device of FIG. 10A showing a seal and a sealing tab for use when the device is formed into a ring and overlapped on itself.

FIG. 10C is a top view of the device of FIG. 10A showing a seal and a sealing tab for use when the device is formed into a ring and overlapped on itself.

FIG. 10D is a bottom view of the device of FIG. 10A showing a seal and a sealing tab for use when the device is formed into a ring and overlapped on itself.

DETAILED DESCRIPTION OF THE INVENTION

Figure 1A:
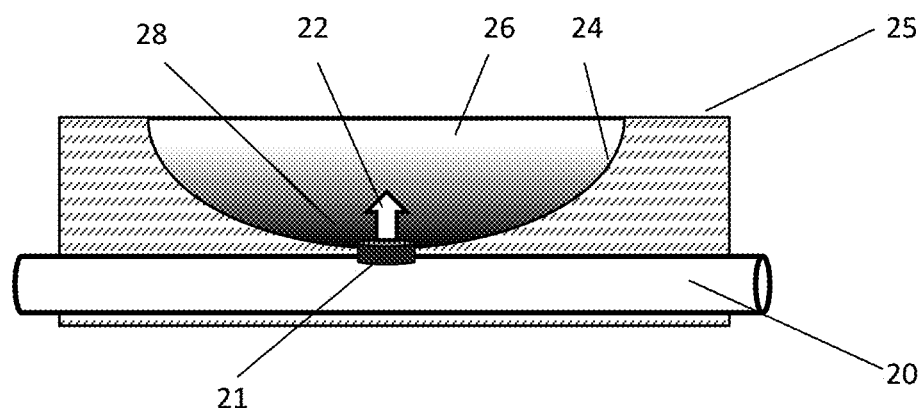
FIG. 1A is a cross-sectional view of an abdominal wound with an intestinal fistula or ostomy that has fouled the wound filler dressing.

Embodiments of the present disclosure provide various embodiments of intestinal fistula and ostomy healing devices, configured for application around a fistula, ostomy, or other wound to physically separate the fistula or ostomy from the remainder of the wound bed area, such that any effluent from the intestine or bowel, or other enteric substances, that pass through the fistula or ostomy are prevented from communicating with the wound bed area.

All of the devices have a flexible fluid containment lineal strip, fluid containment walls which collapse when pressure is applied to the wound dressing, means for forming the lineal strip into any open or closed shape to fit wounds of various shape and size, means for joining the lineal strip to create shaped containment areas, means for creating a seal at the wound bed interface whereby effluent is contained, and means for interfacing with a pouch appliance to capture effluent and bowel contents until bowel contents can be emptied into a toilet.

The device is collapsible, from a first height to a second height less than the first height. When the device is in a relaxed state (e.g., not installed on a wound), the device has its first height, and when the device is in its collapsed or "use" state (e.g., installed on a wound), the device has its second height. In some embodiments, the first height is at least ½ inch and no more than 5 inches, and more particularly from 1 inch to 2 inches The second height is less than the first height, in some embodiments no more than 1 inch, in other embodiment no more than ½ inch, and in other embodiments no more than ¼ inch. The rigidity and thus collapsibility of the device can be adjusting by modifying the material and thickness of the fluid containment wall, and by including features such as ribs or bellows in the fluid containment wall.

As used herein, "collapse", "collapsible" and variations thereof means that the structure, particularly the side wall structure of the fluid containment lineal strip, folds, falls in, crumbles, or otherwise decreases upon itself. In some embodiments of "collapse", the wall may fold upon itself to form a region that has a doubled wall; however, embodiments where two discrete (unconnected) pieces are slid, telescoped, or otherwise moved in overlapping relation to each other is not considered to be a collapse of the pieces. In some embodiments of "collapse", the wall may compress along the longitudinal axis of the fluid containment wall, thus forming folds, creases and the like in the wall.

In use, the device is placed in a wound bed such that the fluid containment wall surrounds a fistula, ostomy or other wound opening. By being so positioned, the device separates and isolates the fistula from the remainder of the wound bed area. This separation prevents or reduces any intestinal effluent or other enteric substance passing out of the fistula from coming into contact with the wound bed area surrounding the fistula, as the effluent will be at least initially retained within the interior volume of the fluid containment wall. This promotes healing of the wound bed and lowers the chances for infection.

In the following description, reference is made to the accompanying drawings that form a part hereof and in which are shown by way of illustration several specific embodiments. The following reference numbers are used throughout the drawings:

20  intestine
21  intestinal fistula or ostomy
22  intestinal content or effluent
24  wound bed
25  abdominal tissue
26  wound filler dressing (e.g. open cell foam)
28  wound filler dressing (e.g. open cell foam) contaminated with intestinal content or effluent
30  flexible fluid containment lineal strip device
32  end joint for flexible fluid containment lineal strip device
34  end joint seal for flexible fluid containment lineal strip device
36  effluent containment area
40  collapsible fluid containment wall
42  pleats in the fluid containment wall
44  configurable (e.g. can be cut to fit), flexible flange forming the device top surface; appliance interface; seating area for pouch appliances that capture intestinal fistula, stoma and wound effluent or bowel contents
46  configurable (e.g. can be cut to fit), flexible flange forming the device base
48  configurable (e.g. can be cut to fit), flexible skirt extending from the device base
49  open cell foam or other wound dressing material
50  flat fluid containment wall
51  curved fluid containment wall
52  ribbing in the fluid containment wall
53  bellows in the fluid containment wall
54  device without skirt along device base
55  plurality of configurable (e.g. can be cut to fit), flexible skirts along device base
56  configurable (e.g. can be cut to fit), flexible flange along interior fluid containment wall base
57  moldable, formable component (e.g. wire or bar)
60  device without open cell foam or other wound dressing material
61  device with rounded open cell foam or other wound dressing material
62  device with angular open cell foam or other wound dressing material
63  unitary embodiment of flexible fluid containment lineal strip device
64  impermeable surface to liquid and air
65  permeable surface to liquid and air
66  barb(s), ridge(s), or bump(s) to retain open cell foam or other wound dressing material
67  flexible bulb seal, solid or hollow, along device base
68  adhesive backing to retain open cell foam or other wound dressing -continued

| | material |
|---|---|
| 70 | cuts or cut lines in flange on device top surface |
| 72 | cuts or cut lines in flange on device base |
| 80 | pleats or folds in flange on device top surface |
| 82 | pleats or folds in flange on device base |
| 90 | stretchable or moldable sections in flange on device top surface |
| 92 | stretchable or moldable sections in flange on device base |
| 100 | angled or curved, configurable (e.g., can be cut to fit), and flexible skirt forming the device base |
| 110 | tab(s) to land on skin and form a seal with skin |
| 112 | curved or angled side(s) to land on edge of wound and form seal with tissue |
| 120 | skin seal comprised of, e.g., hydrocolloid, silicone, etc. |
| 122 | wound seal comprised of, e.g., hydrocolloid, silicone, etc. |
| 130 | seal comprised of, e.g., hydrocolloid, silicone, etc. for use when device is formed into a ring and overlapped on itself |
| 132 | sealing tab for use when device is formed into a ring and overlapped on itself |

The following description provides additional specific embodiments. It is to be understood that other embodiments are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples provided below.

Unless otherwise indicated, all numbers expressing feature sizes, amounts, and physical properties are to be understood as being modified by the term "about." Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

FIG. 1A shows a cross-sectional view of an abdominal wound with an intestinal fistula or ostomy 21 that has fouled a wound filler dressing 26. The intestinal fistula or ostomy 21 communicates intestinal content or effluent 22 from an intestine 20 onto an open wound bed 24 that is surrounded by intact abdominal tissue 25. Common treatment includes the placement of wound filler dressing (e.g. open cell foam) 26 in a wound bed 24 to promote healing. However, intestinal content or effluent 22 contaminates the wound filler dressing 26 causing dressing failure due to intestinal fistula effluent fouling.

Figure 1B:
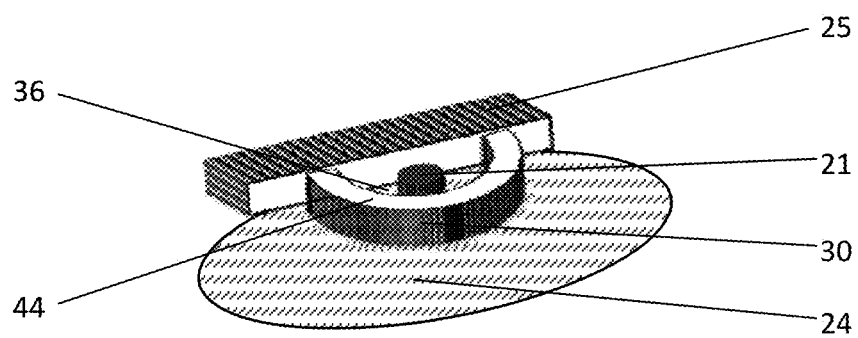
FIG. 1B is a perspective view of the employment of a device according to this disclosure, formed in an open shape (i.e. line, arc, or angle) to isolate an intestinal fistula or ostomy at the edge of a wound bed.

In an embodiment, FIG. 1B shows a first employment of a containment device 30 for treatment of intestinal fistulas and complex wounds. The flexible fluid containment lineal strip device 30 is formed in an open shape (i.e. line, arc, or angle) to isolate an intestinal fistula or ostomy 21 which is positioned at the edge of a wound bed 24 and is adjacent to intact abdominal tissue 25. The flexible fluid containment lineal strip device 30 is cut to length and formed to create a closed effluent containment area 36 between the device 30 and intact abdominal tissue 25. After the intestinal fistula or ostomy 21 is isolated, wound filler dressing (e.g. open cell foam) is placed in the surrounding wound bed 24. The surrounding wound filler dressing and flexible fluid containment lineal strip device 30 are together fixed in place with a covering adhesive wound drape membrane or other mechanism, and negative pressure or vacuum is typically initiated to compress the device 30 and wound filler dressing. Typically, an effluent collection pouch appliance is then adhesively bonded to appliance interface surface 44 to capture effluent and bowel contents from the intestinal fistula or ostomy 21. The pouch appliance can then be emptied into a toilet as needed.

Figure 1C:
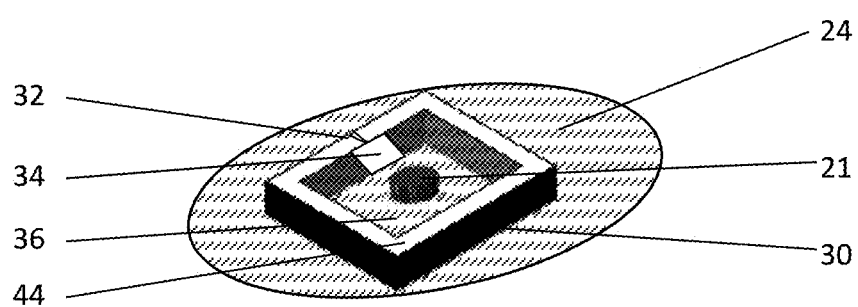
FIG. 1C is a perspective view of an alternative employment of a device according to this disclosure, formed and joined in a closed shape (i.e. circle, ellipse, or polygon) to isolate an intestinal fistula or ostomy near the center of a wound bed.

FIG. 1C shows a second employment of a containment device 30 for treatment of intestinal fistulas and complex wounds. The flexible fluid containment lineal strip device 30 is formed in a closed shape (i.e. circle, ellipse, or polygon) with overlapping or abutting joined end 32 to isolate an intestinal fistula or ostomy 21 near the center of a wound bed 24. The flexible fluid containment lineal strip device 30 is cut to length and formed to create a closed effluent containment area 36. The end joint 32 of the device 30 is joined with adhesive, tape, staples, sutures (e.g. bioabsorbable), interlocking or overlapping end profiles, or other means and the end joint seal 34 can be made with adhesive, tape, or other impermeable means. After the intestinal fistula or ostomy 21 is isolated, wound filler dressing (e.g. open cell foam) is placed in the surrounding wound bed 24. The surrounding wound filler dressing and flexible fluid containment lineal strip device 30 are together fixed in place with an adhesive wound drape membrane or other mechanism, and negative pressure or vacuum is typically initiated to compress the device 30 and wound filler dressing. Typically, an effluent collection pouch appliance is then adhesively bonded to appliance interface surface 44 to capture effluent and bowel contents from the intestinal fistula or ostomy 21. The pouch appliance can then be emptied into a toilet as needed.

Figure 2C:
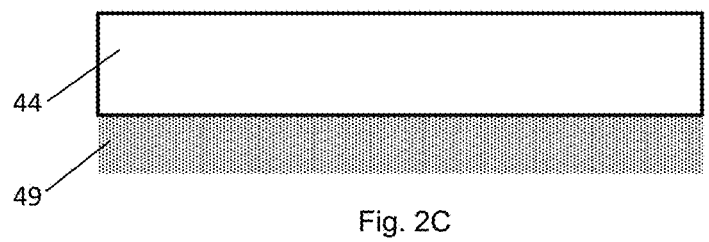
FIG. 2C is a top view of the device of FIG. 2A.
Figure 2B:
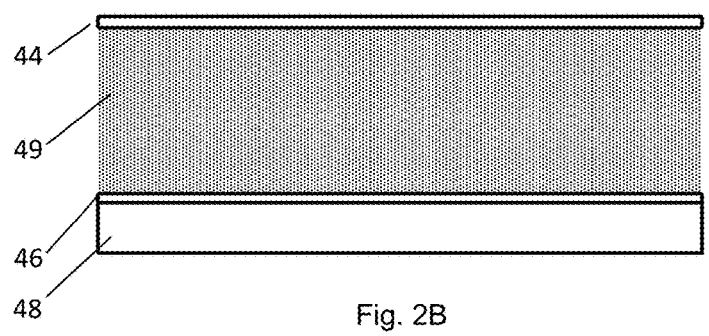
FIG. 2B is an elevational view of an exterior sidewall of the device of FIG. 2A.
Figure 2A:
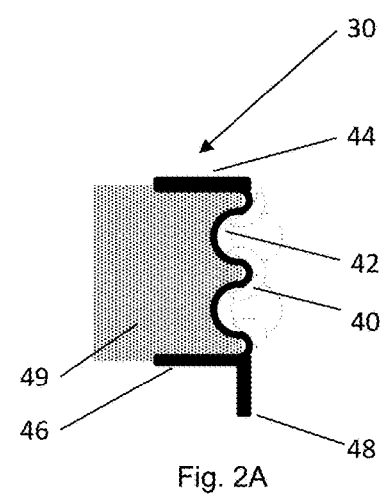
FIG. 2A is a cross-sectional elevational view of an embodiment of a device according to this disclosure.
Figure 2D:
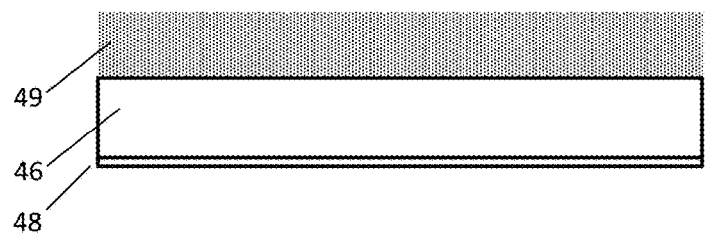
FIG. 2D is a bottom view of the device of FIG. 2A.
Figure 3A:
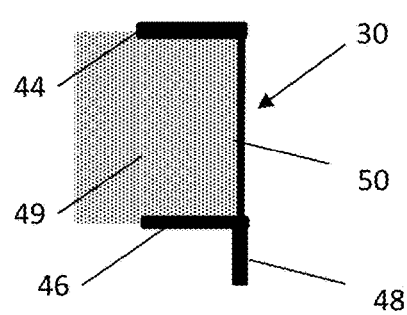
FIG. 3A is a cross-sectional view of an alternative embodiment of the device of FIG. 2A with a flat fluid containment wall.
Figure 3B:
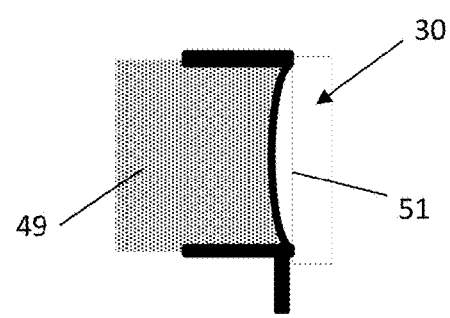
FIG. 3B is a cross-sectional view of an alternative embodiment of the device of FIG. 2A with a curved fluid containment wall.
Figure 3C:
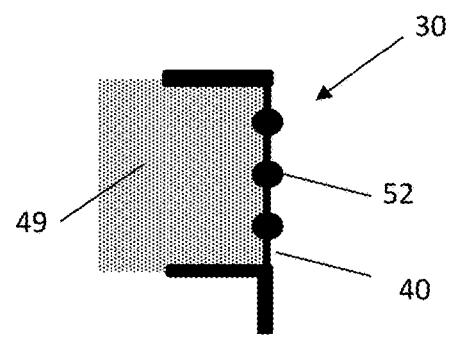
FIG. 3C is a cross-sectional view of an alternative embodiment of the device of FIG. 2A with ribbing in the fluid containment wall.
Figure 3D:
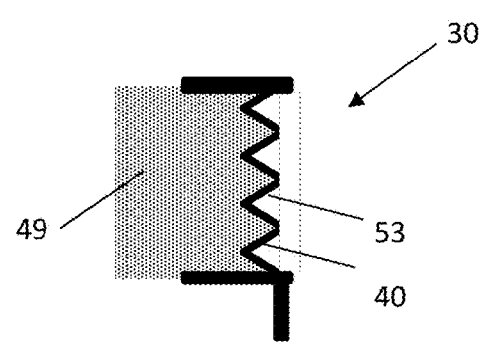
FIG. 3D is a cross-sectional view of an alternative embodiment of the device of FIG. 2A with bellows in the fluid containment wall.
Figure 3E:
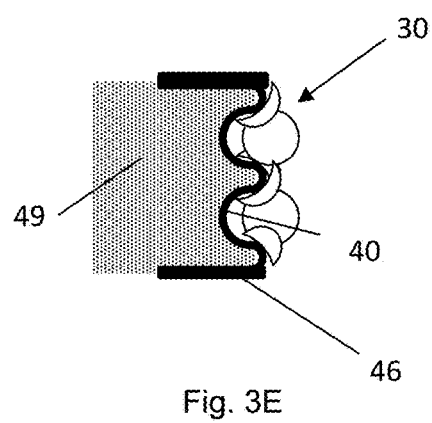
FIG. 3E is a cross-sectional view of an alternative embodiment of the device of FIG. 2A without a skirt along the base of the device.
Figure 3F:
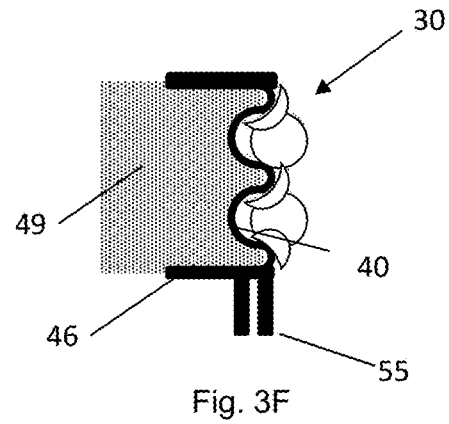
FIG. 3F is a cross-sectional view of an alternative embodiment of the device of FIG. 2A with a plurality of configurable, flexible skirts extending from the base of the device.
Figure 3G:
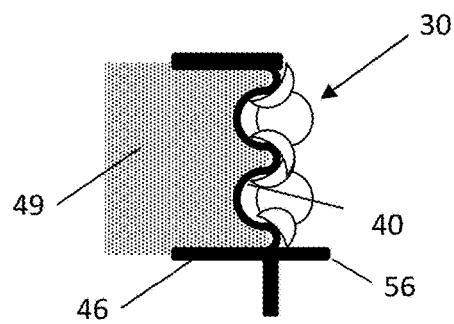
FIG. 3G is a cross-sectional view of an alternative embodiment of the device of FIG. 2A with a configurable, flexible flange along the interior fluid containment wall base.
Figure 3H:
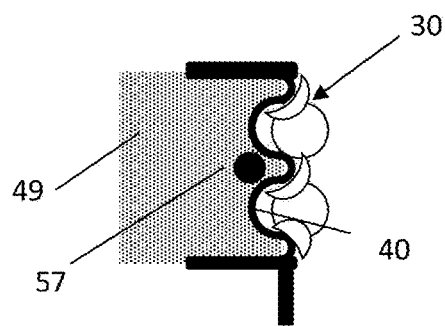
FIG. 3H is a cross-sectional view of an alternative embodiment of the device of FIG. 2A with a moldable, formable component.
Figure 3I:
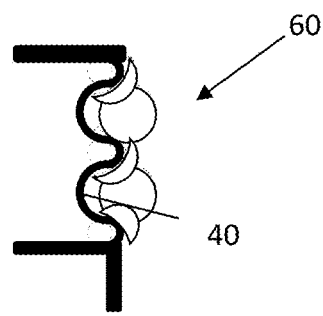
FIG. 3I is a cross-sectional view of an alternative embodiment of the device of FIG. 2A without open cell foam or other wound dressing material.
Figure 3J:
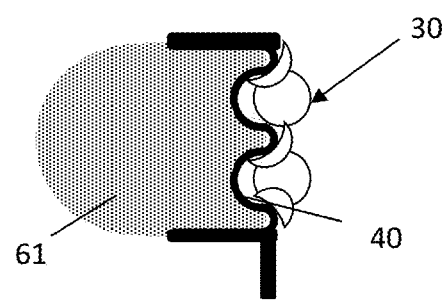
FIG. 3J is a cross-sectional view of an alternative embodiment of the device of FIG. 2A with rounded open cell foam or other wound dressing material.
Figure 3K:
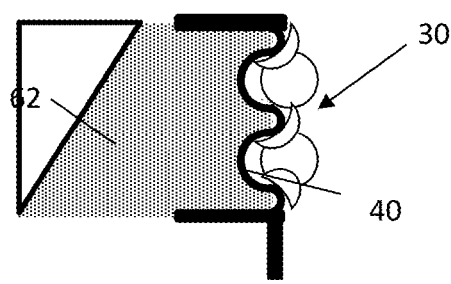
FIG. 3K is a cross-sectional view of an alternative embodiment of the device of FIG. 2A with angular open cell foam or other wound dressing material.
Figure 3L:
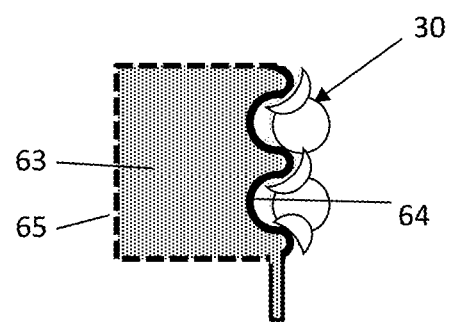
FIG. 3L is a cross-sectional view of an alternative embodiment of the device of FIG. 2A with one-piece construction.
Figure 3M:
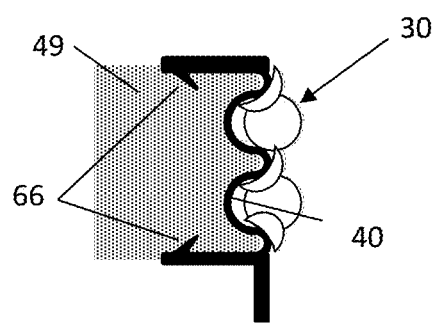
FIG. 3M is a cross-sectional view of an alternative embodiment of the device of FIG. 2A with barb(s), ridge(s), or bump(s) to retain open cell foam or other wound dressing material.
Figure 3N:
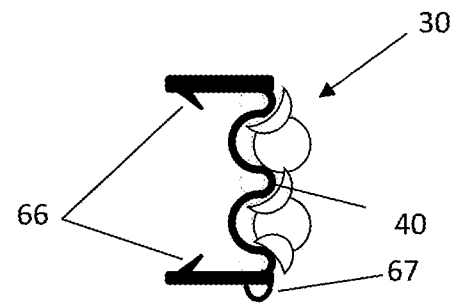
FIG. 3N is a cross-sectional view of an alternative embodiment of the device of FIG. 2A with a bulb seal along the base of the device.
Figure 3P:
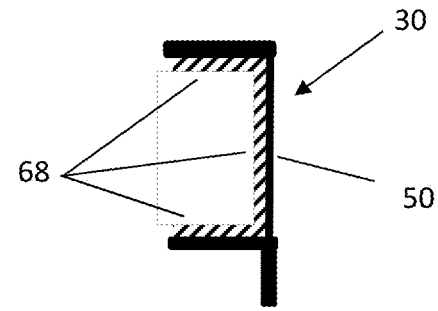
FIG. 3P is a cross-sectional view of an alternative embodiment of the device of FIG. 2A with an adhesive to retain open cell foam or other wound dressing material.

FIG. 2A shows a first embodiment of a containment device 30 for treatment of intestinal fistulas and complex wounds in cross section. FIG. 2B is an outer elevation view of the device 30 and wound dressing material 49 of FIG. 2A, FIG. 2C is a top view of the device 30 of FIG. 2A, and FIG. 2D is a bottom view of the device 30 of FIG. 2A. The flexible fluid containment lineal strip device 30 has a collapsible fluid containment sidewall 40 with pleats 42 to facilitate uniform collapse of the device 30 when compressed. A configurable (e.g. can be cut to fit), flexible flange 44 extending outwardly from a top end of sidewall 40 forms the device top surface and functions as an appliance interface for seating pouch appliances that capture fistula, stoma and wound effluent. A configurable (e.g. can be cut to fit), flexible flange 46 extending outwardly from a bottom end of sidewall 40 forms the device base and is designed to seat the device 30 in the wound bed 24 to create a positive seal at the wound bed interface whereby effluent is contained. The surface of flange 46 may be textured to help seat device 30 in wound bed 24 and mitigate need for separate wound adhesives. Flange 46 can be custom cut (e.g., at bedside) to adapt device 30 to fit irregular wound beds. A configurable (e.g. can be cut to fit), flexible skirt 48 extending downwardly from flange 46 from an inside edge, either perpendicular thereto (as shown in 2A) or at an angle (as described in later embodiments), is a secondary means for creating a seal at the wound bed interface to contain effluent. Skirt 48 may be custom cut for each patient (e.g., at bedside) to adapt device 30 to best fit irregular fistula or wound walls and mechanically block effluent from being drawn past device 30 and contaminating the surrounding wound dressing. Skirt 48 further creates a positive seal with the wound bed to contain effluent and direct it away from the fistula or wound and other nearby tissue to promote healing. And further, skirt 48 isolates the fistula or wound from negative pressure or vacuum. A strip of open cell foam or other wound dressing material 49 is attached to the outside of the device 30 and interfaces with surrounding wound filler dressing. Device 30 may include any or all of the following optional features shown as alternative embodiments in FIGS. 3A, 3B, 3C, 3D, 3E, 3F, 3G, 3H, 3I, 3J, 3K, 3L, 3M, 3N and 3P. FIG. 3A shows the device 30 with a flat fluid containment sidewall 50, upper flange 44, lower flange 46, and optional skirt 48. Optional wound dressing 49 can be attached to an exterior surface of sidewall 50. FIG. 3B shows the device 30 with a curved or convex fluid containment sidewall 51 with optional wound dressing 49; however concave curves can also be contemplated. FIG. 3C shows the device 30 with ribbing 52 in the fluid containment wall 40, and optional wound dressing 49 coupled to sidewall 40. FIG. 3D shows the device 30 with bellows 53 in the fluid containment sidewall 40, and optional wound dressing 49 coupled to sidewall 40. FIG. 3E shows the device 30 with a pleated fluid containment sidewall 40 and no skirt extending from lower flange 46, and optional wound dressing 49 coupled to sidewall 40. FIG. 3F shows the device 30 with a pleated fluid containment sidewall 40, and a plurality of configurable, flexible skirts 55 extending from flange 46 of device 30, and optional wound dressing 49 coupled to sidewall 40. FIG. 3G shows the device 30 with a pleated fluid containment sidewall 40, and a configurable, flexible flange 56 extending inwardly from an interior of the fluid containment sidewall 40, that is substantially coplanar with outwardly extending lower flange 46. Device 30 includes optional wound dressing 49 coupled to sidewall 40. FIG. 3H shows the device 30 with a pleated fluid containment sidewall 40, and a moldable, formable reinforcing component 57, for example, a length of wire or plastic or metal bar coupled to or embedded in sidewall 40 which holds device 30 in a desired form when bent to shape. Device 30 includes optional wound dressing 49 coupled to sidewall 40. FIG. 3I shows a device 60 with a pleated fluid containment sidewall 40 and no open cell foam or other wound dressing material. FIG. 3J shows the device 30 with a pleated fluid containment sidewall 40 and a rounded strip of open cell foam or other wound dressing material 61 attached coupled to sidewall 40. FIG. 3K shows the device 30 with a pleated fluid containment sidewall 40 and an angular strip of open cell foam or other wound dressing material 62 coupled to sidewall 40. FIG. 3L shows the device 30 with a pleated fluid containment sidewall 40 formed of a compressible unitary member 63 with exterior fluid containment surface(s) 65 impermeable to liquid and air, and an interior surface 64 permeable to liquid and air. FIG. 3M shows the device 30 with a pleated fluid containment sidewall 40, and barb(s), ridge(s), and/or bump(s) 66 on an inward facing surface of one or both of flanges 44 and 46, to retain open cell foam or other wound dressing material 49 against sidewall 40 and between flanges 44, 46. FIG. 3N shows the device 30 with a pleated fluid containment sidewall 40, and a flexible bulb seal 67, either solid or hollow, extending from bottom of lower flange 46 as a secondary means for creating a seal at the wound bed interface to contain effluent. Optionally, device 30 can include barb(s), ridge(s), and/or bump(s) 66, similar to the embodiment shown in FIG. 3M. FIG. 3P shows the device 30 with a linear fluid containment sidewall 50 with adhesive backing 68 to retain open cell foam or other wound dressing material (not shown) between flanges 44, 46 and sidewall 50.

Any of these various options shown as alternative embodiments in FIGS. 3A, 3B, 3C, 3D, 3E, 3F, 3G, 3H, 3I, 3J, 3K, 3L, 3M, 3N, and 3P may be used alone or in any combination on device 30. For exemplary purposes only, sidewall 40 in FIGS. 3F-3N depict a pleated sidewall as shown in FIG. 3E. One of ordinary skill in the art would recognize that sidewall 40 and pleats 46 can be substituted for the sidewalls and features of any of the other embodiments of FIGS. 3A-3D, with no limitation. Similarly, flange arrangements 44, 46 with or without skirt 48 and/or barbs 66 and/or bulb 67 can be arranged in any manner contemplated.

Figure 4C:
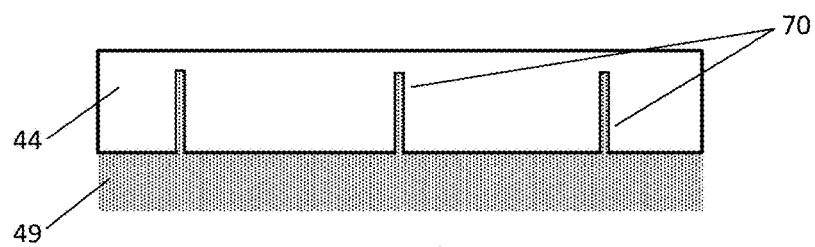
FIG. 4C is a top view of the device of FIG. 4A showing cuts or cut lines in the top flange of the device.
Figure 4B:
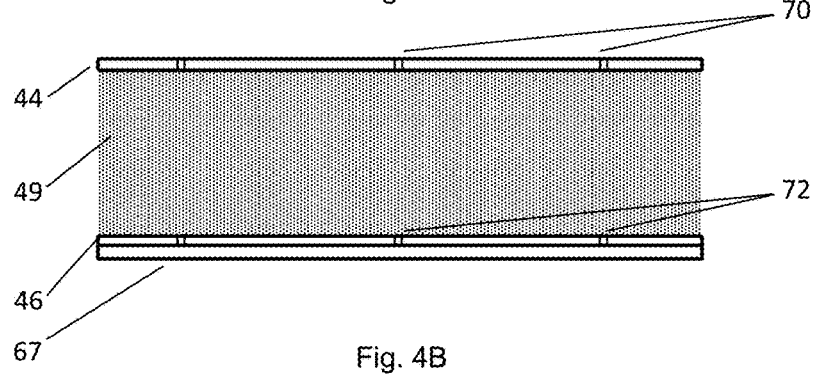
FIG. 4B is an elevational view of an exterior sidewall of the device of FIG. 4A showing cuts or cut lines in both the top and bottom flanges of the device.
Figure 4A:
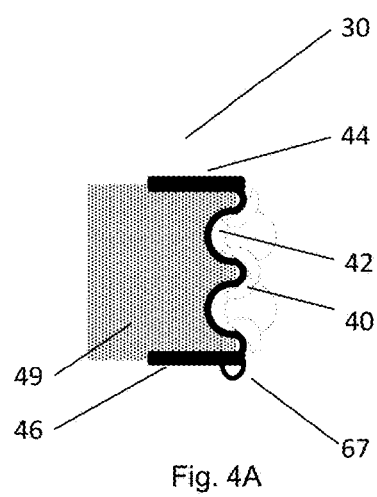
FIG. 4A is a cross-sectional elevational view of an alternative embodiment of the device of FIG. 2A.
Figure 4D:
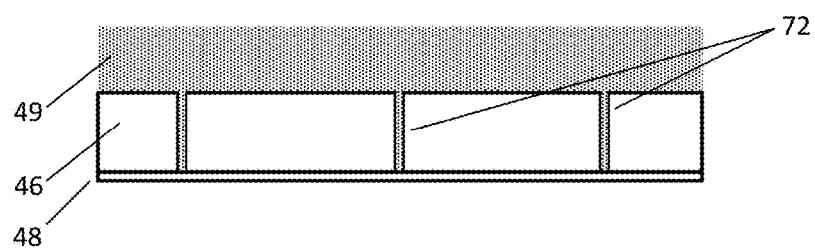
FIG. 4D is a bottom view of the device of FIG. 4A showing cuts or cut lines in the bottom flange of the device.
Figure 5C:
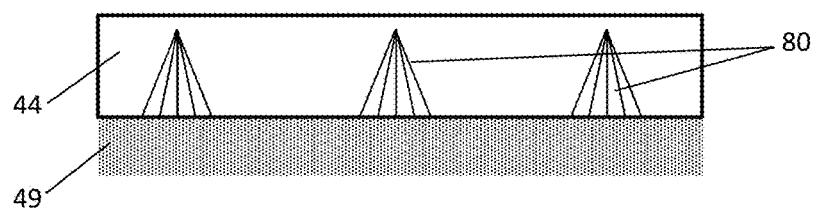
FIG. 5C is a top view of the device of FIG. 5A showing pleats or folds in the top flange of the device.
Figure 5B:
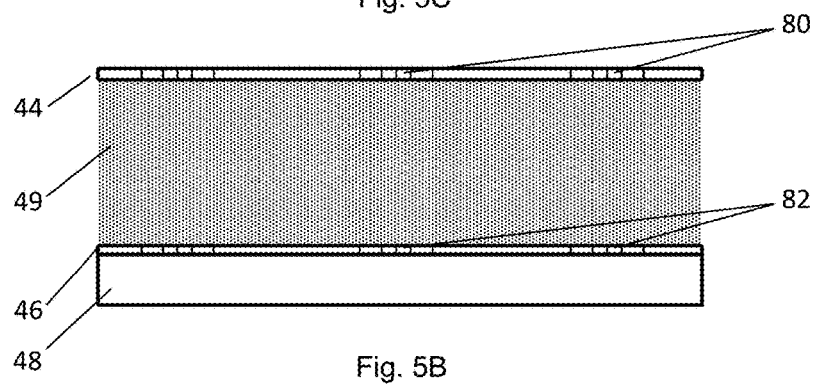
FIG. 5B is an elevational view of an exterior sidewall of the device of FIG. 5A showing pleats or folds in both the top and bottom flanges of the device.
Figure 5A:
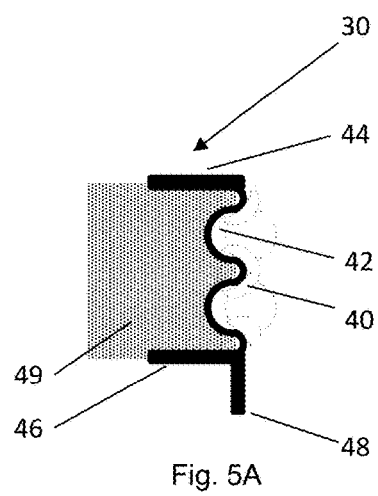
FIG. 5A is a cross-sectional elevational view of an alternative embodiment of the device of FIG. 2A.
Figure 5D:
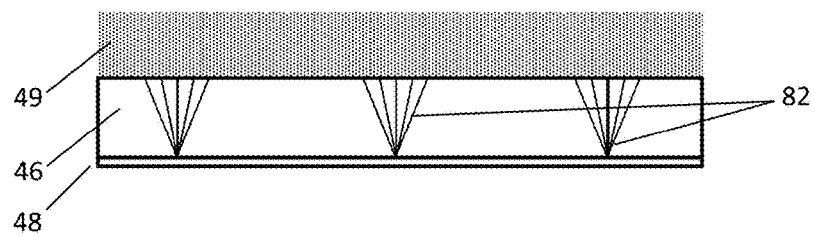
FIG. 5D is a bottom view of the device of FIG. 5A showing pleats or folds in the bottom flange of the device.
Figure 6C:
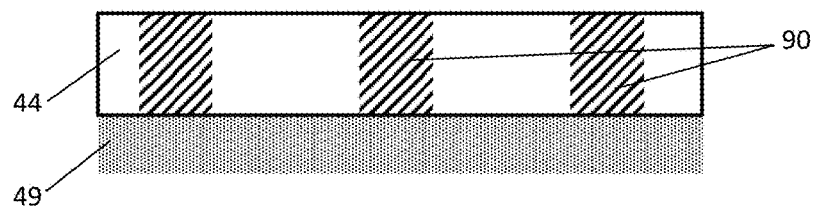
FIG. 6C is a top view of the device of FIG. 6A showing stretchable or moldable sections in the top flange of the device.
Figure 6B:
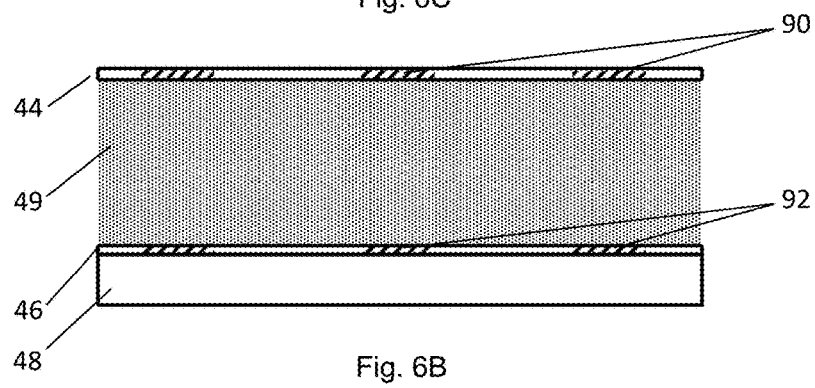
FIG. 6B is an elevational view of an exterior sidewall of the device of FIG. 6A showing stretchable or moldable sections in both the top and bottom flanges of the device.
Figure 6A:
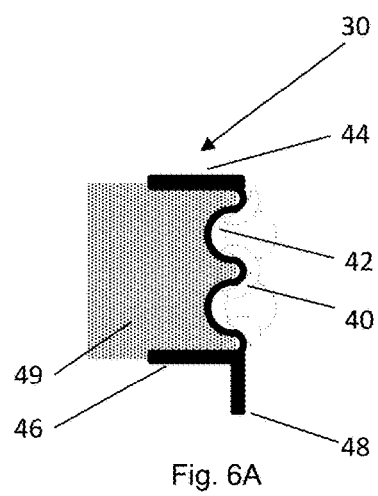
FIG. 6A is a cross-sectional elevational view of an alternative embodiment of the device of FIG. 2A.
Figure 6D:
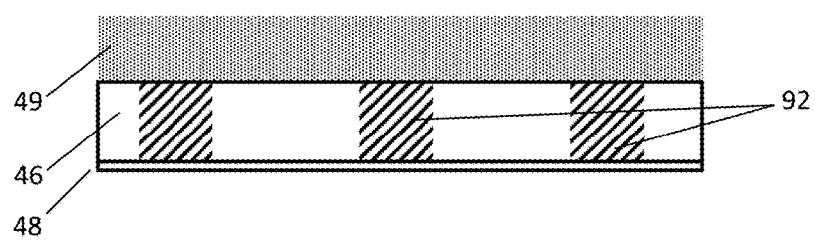
FIG. 6D is a bottom view of the device of FIG. 6A showing stretchable or moldable sections in the bottom flange of the device.

Device 30 can also include any or all of the following optional features shown as alternative embodiments in FIGS. 4A, 4B, 4C and 4D, FIGS. 5A, 5B, 5C and 5D, and FIGS. 6A, 6B, 6C and 6D which can aid in its flexiblity and confirmity to the wound bed. FIGS. 4B and 4C show structure defining cuts or cut lines 70 in the configurable flexible upper or top flange 44 of device 30. FIGS. 4B and 4D show cuts or cut lines in the configurable flexible lower or bottom flange 46 of device 30. FIGS. 5B and 5C show pleats or folds 80 in the configurable flexible upper or top flange 44 of device 30. FIGS. 5B and 5D show pleats or folds 82 in the configurable flexible lower or bottom flange 46 of device 30. FIGS. 6B and 6C show stretchable or moldable sections 90 in the configurable flexible upper or top flange 44 of device 30. FIGS. 6B and 6D show stretchable or moldable sections 92 in the configurable flexible lower or bottom flange 46 of device 30.

Any of these various options shown as alternative embodiments in FIGS. 4A, 4B, 4C and 4D, FIGS. 5A, 5B, 5C and 5D, and FIGS. 6A, 6B, 6C and 6D may be used alone or in any combination on device 30 as a mechanism for forming the device 30 into open or closed shapes to fit wounds of various shape and size. In addition, although sidewall 40 is depicted as a pleated sidewall in FIGS. 4A, 5A, and 6A, any of the alternative previously described sidewalls can be substituted for the pleated sidewall, with or without a reinforcing member (e.g. 57 in FIG. 3H). Skirt 48 (if present) can comprise a single skirt (as shown in FIGS. 5A and 6A) extending below flange 48, can comprise multiple skirts as depicted in FIG. 3F, or no skirt at all. Finally, optional open cell foam or wound dressing 49 can be coupled, such as by adhesive, barbs, hooks, or otherwise, as described herein, between flanges 44 and 46 and to an exterior surface of sidewall 40.

Figure 7C:
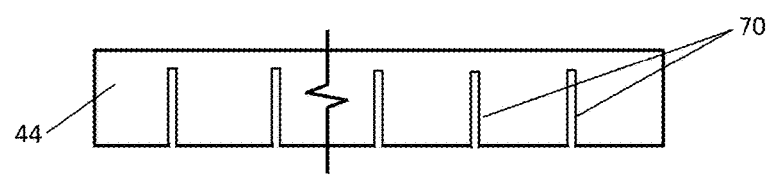
FIG. 7C is a top view of the device of FIG. 7A showing cuts or cut lines in the top flange of the device.
Figure 7B:
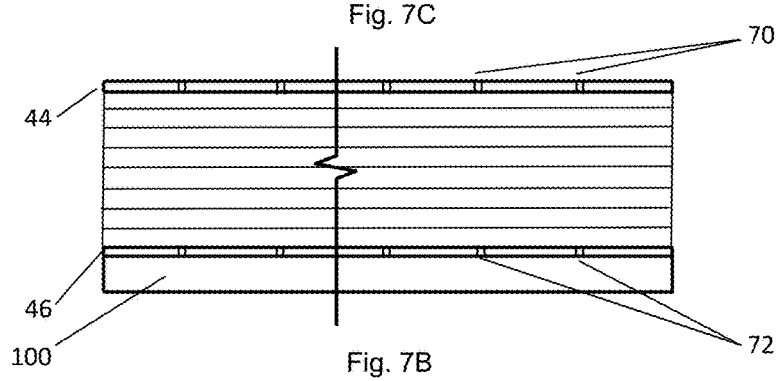
FIG. 7B is an elevational view of an exterior sidewall of the device of FIG. 7A.
Figure 7A:
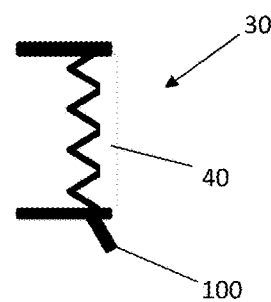
FIG. 7A is a cross-sectional elevational view of an alternative embodiment of the device of FIG. 2A showing an angled or curved skirt extending from the bottom flange of the device.
Figure 7D:
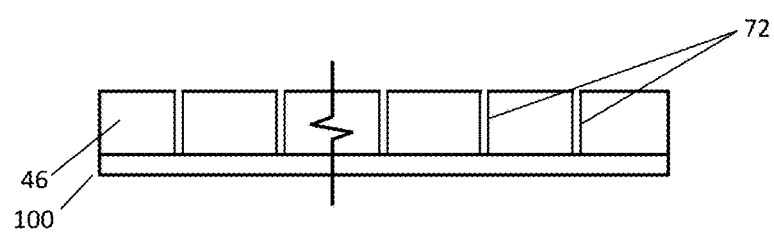
FIG. 7D is a bottom view of the device of FIG. 7A showing cuts or cut lines in the bottom flange of the device.

Device 30 can also include any or all of the following optional features shown as alternative embodiments in FIGS. 7A, 7B, 7C, and 7D; FIGS. 8A, 8B, 8C, and 8D; FIGS. 9A, 9B, 9C, and 9D; and FIGS. 10A, 10B, 10C, and 10D. FIGS. 7A, 7B, and 7D show an angled or curved, configurable (e.g., can be cut to fit), and flexible skirt 100 extending below and along lower flange 46. In embodiments, skirt 100 extends inwardly and downwardly at an angle from flange 46. In this embodiment, sidewall 40 is bellowed; however any of the sidewall configurations described previously, e.g. pleated, curved, staight, can be substituted for the bellowed sidewall. Similar to the embodiment depicted in FIGS. 4A-4D, flanges 44 and 46 can includes cuts or notches 70, 72, respectively. However, folds or pleats as depicted in FIGS. 5A-5D, and/or stretchable sections as depicted in FIGS. 6A-6D can be substituted for or in addition to notches 70, 72.

Figure 8C:
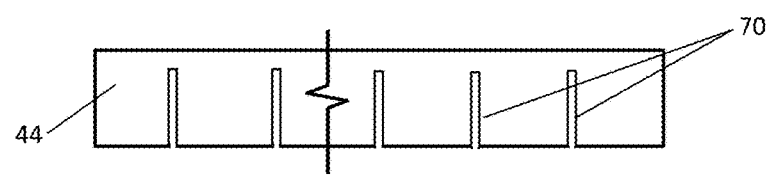
FIG. 8C is a top view of the device of FIG. 8A.
Figure 8B:
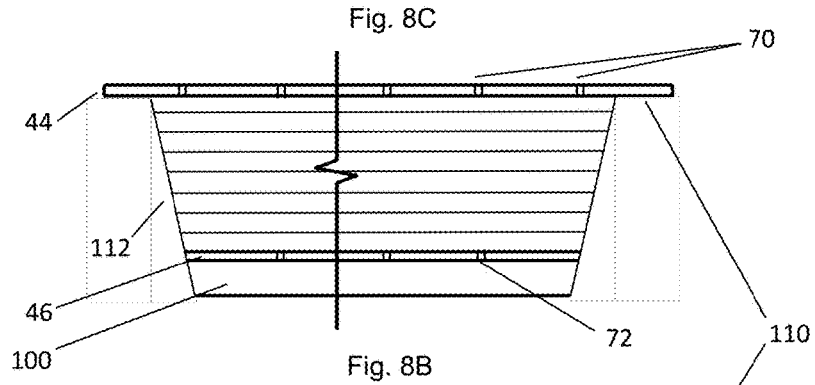
FIG. 8B is an elevational view of an exterior sidewall of the device of FIG. 8A showing tab(s) along the configurable flexible flange on the device top surface to land on skin and form seal with skin and curved or angled sides to land on an edge of wound and form a seal with tissue.
Figure 8A:
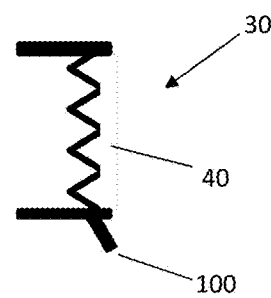
FIG. 8A is a cross-sectional elevational view of an alternative embodiment of the device of FIG. 7A.
Figure 8D:
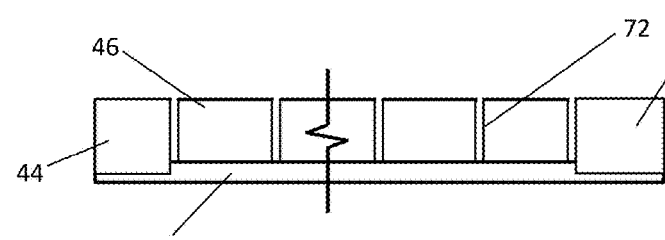
FIG. 8D is a bottom view of the device of FIG. 8A showing tab(s) along the configurable flexible top flange of the device position on the skin to form a seal with the skin.

FIGS. 8B and 8D show tab(s) 110 along the configurable flexible upper or top flange 44 of device 30 that can land on skin and form a seal with skin, such that flange 44 is longer than bottom flange 46. FIG. 8B shows tapered sidewall 112 that can land on an edge of a wound and form a seal with tissue. In this embodiment, sidewall 112 is bellowed; however any of the sidewall configurations described previously, e.g. pleated, curved, staight, can be substituted for the bellowed sidewall. Similar to the embodiment depicted in FIGS. 4A-4D, flanges 44 and 46 can includes cuts or notches 70, 72, respectively. However, folds or pleats as depicted in FIGS. 5A-5D, and/or stretchable sections as depicted in FIGS. 6A-6D can be substituted for or in addition to notches 70, 72. In this embodiment, a single angled skirt 100 is depicted; however, perpendicular skirt 50 and/or multiple skirts as previously described can be substituted for skirt 100.

FIGS. 9A, 9B, and 9D is similar to the embodiment shown in FIGS. 8A-8D, except that in this embodiment, a skin seal 120, which can be comprised of, e.g., hydrocolloid, silicone, etc., is positioned along a bottom surface of the configurable flexible top or upper flange 44 of device 30. Furthermore, as depicted in FIGS. 9B and 9D, a wound seal 122, which can be comprised of, e.g., hydrocolloid, silicone, etc. which extends along one longitudinal edge of sidewall 40. In this embodiment, sidewall 112 is bellowed; however any of the sidewall configurations described previously, e.g. pleated, curved, staight, can be substituted for the bellowed sidewall. Similar to the embodiment depicted in FIGS. 4A-4D, flanges 44 and 46 can includes cuts or notches 70, 72, respectively. However, folds or pleats as depicted in FIGS. 5A-5D, and/or stretchable sections as depicted in FIGS. 6A-6D can be substituted for or in addition to notches 70, 72. In this embodiment, a single angled skirt 100 is depicted; however, perpendicular skirt 50 and/or multiple skirts as previously described can be substituted for skirt 100.

FIGS. 10A, 10B, 10C, and 10D show a seal 130, which can be comprised of, e.g., hydrocolloid, silicone, etc., for use when device is formed into a ring and overlapped on itself. FIGS. 10A, 10B, and 10C show a sealing tab 132 for use when device is formed into a ring and overlapped on itself. In this embodiment, sidewall 112 is bellowed; however any of the sidewall configurations described previously, e.g. pleated, curved, staight, can be substituted for the bellowed sidewall. Similar to the embodiment depicted in FIGS. 4A-4D, flanges 44 and 46 can includes cuts or notches 70, 72, respectively. However, folds or pleats as depicted in FIGS. 5A-5D, and/or stretchable sections as depicted in FIGS. 6A-6D can be substituted for or in addition to notches 70, 72. In this embodiment, a single angled skirt 100 is depicted; however, perpendicular skirt 50 and/or multiple skirts as previously described can be substituted for skirt 100.

Any of these various options shown as alternative embodiments in FIGS. 7A, 7B, 7C, and 7D; FIGS. 8A, 8B, 8C, and 8D; FIGS. 9A, 9B, 9C, and 9D; and FIGS. 10A, 10B, 10C, and 10D may be used alone or in any combination on device 30 as a mechanism for forming the device 30 into open or closed shapes to fit wounds of various shape and size.

The various embodiments of devices described herein may be made of any material suitable for the purposes described above, as will be recognized by those skilled in the art. Thus, in certain embodiments, the containment devices for the treatment of intestinal fistulas and complex wounds, or at least a portion thereof, may be made of any biocompatible materials, for example, plastics or rubber. In one particular embodiment, the fluid containment wall may be a silicone rubber. Other materials may be used, for example, a flexible thermoplastic. Preferably, the fluid containment wall is non-fluid permeable and/or non-porous. Further, as will be recognized by those skilled in the art, the devices can be sized and shaped to accommodate all different sizes and shapes of fistulas and/or wounds.

In embodiments, one or more devices according to the embodiments may be provided as a kit with instructions for use, and optionally with wound dressing material. In an embodiment, the instructions for use can include the following or similar steps for surrounding a fistula, though fewer or additional steps can be provided and the steps can be provided in other orders:

1. Disinfect device per institutional protocol. Locate bulb seal (if present) or skirt (if present) along bottom flange of device. Bulb seal or skirt is designed to be placed DOWN in the wound bed.
2. Cut hole in wound dressing centered over fistula or wound.
3. Insert device around perimeter of dressing hole until it overlaps itself or forms a butt splice. If petals formed in the flanges, cut strip so that at least one full petal overlaps another petal on the opposite end of the strip. Ensure top flange is seated on top of wound dressing and bottom flange is flush with bottom of wound dressing.
4. Prepare wound bed. Place assembled device and dressing onto wound bed so that device opening is centered over fistula or wound opening.
5. Seal entire dressing assembly with clear drape. Begin negative pressure wound therapy if prescribed. Cut drape from inner ring. If seal is lost, try stoma paste inside device base. Apply collection appliance to top flange.

In an embodiment, the instructions for use can include the following or similar steps for walling off a fistula from the rest of a wound bed area, though fewer or additional steps can be provided and the steps can be provided in other orders:

1. Disinfect device per your institutional protocol. Locate bulb seal or skirt along bottom flange of device. Bulb seal or skirt is designed to be placed DOWN in the wound bed.
2. Cut wound dressing to fit wound bed and the isolate fistula or wound opening.
3. Apply device along perimeter of dressing. Cut strip to length required. Ensure top flange is seated on top of wound dressing and bottom flange is flush with bottom of wound dressing.
4. Prepare wound bed. Place assembled device and dressing onto wound bed so that device is between fistula and wound dressing.
5. Seal entire dressing assembly with clear drape. Begin negative pressure wound therapy if prescribed. Cut drape from area over fistula. If seal is lost, try stoma paste inside device base. Apply collection appliance to top flange.

Accordingly, described herein are various embodiments of devices to contain and control the effluent and bowel contents from intestinal fistulas; these devices are adaptable to other fistulas, stomas, and other wound types. Described is, for example, a device to contain and control the effluent of intestinal fistulas, the device comprising: (a) a flexible fluid containment lineal strip, (b) fluid containment walls which collapse when pressure is applied to the wound dressing, (c) means for forming the lineal strip into open or closed shapes to fit wounds of various shape and size, (d) means for joining the lineal strip to create closed effluent containment areas, (e) means for creating a seal at the wound bed interface whereby effluent is contained, and (f) means for interfacing with a pouch appliance to capture effluent and bowel contents.

Additionally, the various embodiments have numerous advantages:
  simple construction so device and dressings can be applied and changed by nonspecialized bedside or homecare nurses;
  positive seals to the wound bed do not allow effluent to be drawn past the seal with NPWT or other wound care techniques which extends dressing life and establishes effective conditions for wound healing;

skirt or bulb seal which aligns device around a fistula or wound and holds device in the intended location with NPWT and other wound therapies during normal daily activity of the patient;

seal design and textured flanges mitigate the need for ostomy adhesive which reduces the frequency of wound dressing changes due to ostomy adhesive failure;

device flanges and skirt can be custom cut at bedside to best fit the device to irregular wound beds and a fistula or wound that is in close proximity to the sides of the wound bed;

devices are flexible and compresses symmetrically when part of NPWT or other wound therapies to prevent deformation or buckling over and related aggravation of the fistula or wound;

devices isolate the fistula or wound from NPWT vacuum thus protecting the bowel or wound site from negative pressures;

devices improve quality of life by allowing patients to return to their normal life and work routines during the healing process Thus, embodiments of the CONTAINMENT DEVICES FOR TREATMENT OF INTESTINAL FISTULAS AND COMPLEX WOUNDS are disclosed. The implementations described above and other implementations are within the scope of the following claims. One skilled in the art will appreciate that the present invention can be practiced with embodiments other than those disclosed, such as, for example, but not limited to, those disclosed in U.S. Pat. No. 9,078,990, entitled "DEVICES AND METHODS FOR TREATMENT OF FISTULAS AND COMPLEX WOUNDS", incorporated herein by reference in its entirety. For example, the device fluid containment wall could have other shapes; flanges could intersect the fluid containment wall at various angles; a plurality of skirts could be added to the length of the fluid containment wall; the skirts could have other cross-sectional shapes with bulbs, fins, ribbing or pleats; the device could be coated or impregnated with chemical or biological material to accelerate wound healing; etc. The disclosed embodiments are presented for purposes of illustration and not limitation, and the present invention is limited only by the claims that follow.

What is claimed is:

1. A customizable device to manage effluent from a wound, the wound including a fistula, ostomy, or wound opening, and a wound bed, by providing a containment boundary to isolate the fistula, ostomy, or wound opening from negative pressure applied to the wound bed, the device comprising:

a trimmable and flexible lineal elongate strip defining a fluid containment wall and having a length, a first end, and a second end, the fluid containment wall being configured to collapse along an axis perpendicular to the length from a first height to a second height less than the first height when subjected to negative pressure, a sealing flange extending from a first longitudinal edge of the fluid containment wall and along at least a portion of the length of the lineal elongate strip;

an appliance interface flange extending from a second longitudinal edge of the fluid containment wall and along at least a portion of the length of the lineal elongate strip;

wherein the device is configured to be positioned in the wound in one of an open shape containment configuration in which the first end and second end of the lineal elongate strip are positioned in the wound bed adjacent to intact tissue such that the device provides a portion of the containment boundary surrounding the fistula, ostomy, or wound opening, and the intact tissue provides a remaining portion of the containment boundary, and a closed shape containment configuration in which the first end and second end of the lineal elongate strip are positioned adjacent to one another and the device provides the entire containment boundary surrounding the fistula, ostomy, or wound opening, and wherein the containment boundary physically isolates the fistula, ostomy, or wound opening within the wound bed.

2. The device of claim 1, wherein the open shape is one of a line, an arc, or an angle, and wherein the closed shape is one of a circle, ellipse, or a polygon.

3. The device of claim 1, wherein either or both of the first end and second end are trimmed to create a seal with the intact tissue in the open shape containment configuration.

4. The device of claim 1, wherein the appliance interface flange includes one or more tabs to create a seal with the intact tissue in the open shape containment configuration.

5. The device of claim 1, further comprising one or more configurable flexible skirts or bulbs depending from the first longitudinal edge of the fluid containment wall, the one or more skirts or bulbs at least partially extending around or within the wound opening to create a seal at a wound bed interface between the wound opening and the wound bed.

6. The device of claim 5, wherein the one or more one or more configurable flexible skirts or bulbs depend from the first longitudinal edge at an angle from the fluid containment wall such that the one or more one or more configurable flexible skirts or bulbs curve or angle inwardly from the fluid containment wall.

7. The device of claim 1, wherein either or both of the sealing flange and the appliance interface flange include a plurality of independently flexible tabs.

8. The device of claim 7, wherein the one or more tabs of either or both of the sealing flange and the appliance interface flange are separated by one or more slits.

9. The device of claim 7, wherein the one or more tabs of either or both of the sealing flange and the appliance interface flange are separated by one or more pleats.

10. The device of claim 7, wherein the one or more tabs of either or both of the sealing flange and the appliance interface flange are separated by one or more sections of stretchable or moldable material.

11. The device of claim 1, wherein either or both of the sealing flange and the appliance interface flange include barbs, ridges, and/or bumps extending therefrom configured to retain wound dressing material coupled to the device.

12. The device of claim 1, wherein any or all of the fluid containment wall, sealing flange, and/or appliance interface flange include an adhesive material on an outer surface thereof, the adhesive material being configured to retain a wound dressing material coupled to the device.

13. The device of claim 1, wherein the fluid containment wall includes structure defining ribs or pleats to facilitate shifting between the first height and the second height.

14. The device of claim 1, further comprising a length of wire or bar coupled to or embedded in the fluid containment wall, the length of wire or bar being configured to hold the strip in a desired form when bent to shape.

15. The device of claim 1, wherein the fluid containment wall is curved or angled inwardly from the appliance interface flange to the sealing flange such that the fluid containment wall is configured to be positioned on an edge of the wound bead to form a seal.

16. The device of claim 1, wherein the sealing flange includes a skin seal formed of hydrocolloid or silicone.

17. The device of claim 1, wherein the fluid containment wall includes a wound seal formed of hydrocolloid or silicone.

18. The device of claim 1, wherein the fluid containment wall includes a sealing tab to seal the device when the device is formed into a ring and overlapped on itself.

19. A method for using a customizable device to manage effluent from a wound, the wound including a fistula, ostomy, or wound opening, and a wound bed, by providing a containment boundary to isolate the fistula, ostomy, or wound opening from negative pressure applied to the wound bed, the method comprising:

provided the device comprising:

a trimmable and flexible lineal elongate strip extending defining a fluid containment wall and having a length, a first end, and a second end, the fluid containment wall being configured to collapse along an axis perpendicular to the length from a first height to a second height less than the first height when subjected to negative pressure, a sealing flange extending from a first longitudinal edge of the fluid containment wall and along at least a portion of the length of the lineal elongate strip;

an appliance interface flange extending from a second longitudinal edge of the fluid containment wall and along at least a portion of the length of the lineal elongate strip;

positioning the device in the wound in one of an open shape containment configuration comprising a line, angle, or arc in which the first end and second end of the lineal elongate strip are positioned in the wound bed adjacent to intact tissue, the device provides a portion of the containment boundary surrounding the fistula, ostomy, or wound opening, and the intact tissue provides a remaining portion of the containment boundary, and a closed shape containment configuration comprising a circle, an ellipse, or a polygon in which the first end and second end of the lineal elongate strip are positioned adjacent to one another and the device provides the entire containment boundary surrounding the fistula, ostomy, or wound opening;

sealing the containment boundary, such that the fistula, ostomy, or wound opening are physically isolated within the wound bed; and applying negative pressure to collapse the interior fluid containment wall from the first height to the second height.

20. A kit comprising:

a device to manage effluent drainage from a wound, the wound including a wound opening and a wound bed surrounding the wound opening, the device comprising— an elongate strip defining a sidewall, the sidewall being configured to collapse from a first height to a second height less than the first height, a sealing flange extending from a first longitudinal edge of the sidewall, and an appliance interface flange extending from a second longitudinal edge of the sidewall;

a length of wound dressing coupled to the sidewall of the device; and instructions indicating administration by cutting the strip to a length sufficient to at least partially surround the wound opening, manipulating the strip to a shape conforming to the wound opening such that the wound sealing flange is flush with the wound bed, the attached wound dressing fills the wound bed, and the appliance interface flange is flush with a top surface of the wound dressing opposite the wound sealing flange, and positioning the device with attached wound dressing in the wound such that the sidewall of the strip isolates the fistula from the attached wound dressing.

* * * * *